(12) United States Patent
Liberkowski

(10) Patent No.: US 9,801,700 B1
(45) Date of Patent: Oct. 31, 2017

(54) DENTAL PROSTHESIS WITH SEALED ATTACHMENT INTERFACE AND CLEANING FLUID ACCESS THERETO

(71) Applicant: Janusz Liberkowski, Los Gatos, CA (US)

(72) Inventor: Janusz Liberkowski, Los Gatos, CA (US)

(73) Assignee: Janusz Liberkowski, Los Gatos, CA (US)

( * ) Notice: Subject to any disclaimer, the term of this patent is extended or adjusted under 35 U.S.C. 154(b) by 206 days.

(21) Appl. No.: 14/543,679

(22) Filed: Nov. 17, 2014

(51) Int. Cl.
*A61C 13/01* (2006.01)
*A61C 8/00* (2006.01)
*A61C 17/02* (2006.01)

(52) U.S. Cl.
CPC ............ *A61C 13/01* (2013.01); *A61C 8/0077* (2013.01); *A61C 17/02* (2013.01)

(58) Field of Classification Search
CPC ......... A61C 13/01; A61C 8/00; A61C 8/0027; A61C 8/003; A61C 8/0048; A61C 13/08; A61C 13/00; A61C 13/225; A61C 13/24; A61C 13/245
USPC ........................................... 433/199.1, 201.1
See application file for complete search history.

(56) References Cited

U.S. PATENT DOCUMENTS

| | | | | |
|---|---|---|---|---|
| 1,202,971 A * | 10/1916 | Daiber | ................. | A61C 13/245 433/185 |
| 1,754,058 A * | 4/1930 | Smith | .................... | A61C 13/00 433/199.1 |
| 2,036,715 A * | 4/1936 | Morgan | ................. | A61C 13/00 433/168.1 |
| 2,070,771 A * | 2/1937 | Artzt | ....................... | A61C 13/00 264/18 |
| 2,911,720 A * | 11/1959 | Greenmun | ............. | A61C 13/28 433/169 |
| 3,503,127 A * | 3/1970 | Kasdin | .................... | A61C 13/24 433/199.1 |
| 3,514,858 A * | 6/1970 | Silverman | ............ | A61C 8/0022 433/171 |
| 3,748,739 A * | 7/1973 | Thibert | ................ | A61C 13/275 433/173 |
| 3,750,287 A * | 8/1973 | Bloom | ..................... | A61C 13/25 433/185 |
| 3,787,974 A * | 1/1974 | Gaylord | ................. | A61C 13/25 433/185 |
| 3,889,374 A * | 6/1975 | Saffir | ...................... | A61K 6/083 433/199.1 |
| 3,921,292 A * | 11/1975 | Ivchenko | ............... | A61C 13/00 433/199.1 |
| 4,085,506 A * | 4/1978 | Lew | ..................... | A61C 8/0048 433/172 |

(Continued)

*Primary Examiner* — Alvin Stewart

(57) ABSTRACT

A dental prosthesis has a gum sealing rim that snugly contacts the patient's gum. The cavity formed within the gum sealing rim is accessed by through holes via which a pressurized cleaning fluid may be injected into the cavity. The cleaning fluid swirls around and washes of bacteria and deposits. Through a number of cleaning fluid drains, the cleaning fluid exits again the cavity. An additional drain blocker may be configured such that it blocks the cleaning fluid drains while it is clamped by the patient between the teeth. The resulting pressure build up in the cavity causes the cleaning fluid to squeeze out and clean the sealing interface between the gum sealing rim and the patient's gum.

13 Claims, 5 Drawing Sheets

(56) References Cited

U.S. PATENT DOCUMENTS

| | | | | |
|---|---|---|---|---|
| 4,182,034 | A * | 1/1980 | McCauley | A61C 8/00 433/174 |
| 4,488,875 | A * | 12/1984 | Niznick | A61C 8/00 433/173 |
| 4,767,328 | A * | 8/1988 | Branemark | A61C 8/0048 433/168.1 |
| 4,784,608 | A * | 11/1988 | Mays | A61C 8/0048 433/172 |
| 5,249,962 | A | 10/1993 | Ascher | |
| 5,324,198 | A * | 6/1994 | Hazen | A61C 13/24 433/167 |
| 5,427,906 | A * | 6/1995 | Hansen | A61C 8/0048 433/173 |
| 5,431,563 | A * | 7/1995 | Huybrechts | A42B 3/12 128/862 |
| 5,503,557 | A * | 4/1996 | Sillard | A61C 13/0015 433/172 |
| 5,513,988 | A * | 5/1996 | Jeffer | A61C 13/0025 433/168.1 |
| 5,678,993 | A * | 10/1997 | Jeffer | A61C 8/00 433/168.1 |
| 5,885,077 | A * | 3/1999 | Jeffer | A61C 8/00 433/168.1 |
| 6,244,869 | B1 * | 6/2001 | Billet | A61C 13/0003 433/199.1 |
| 6,506,052 | B1 * | 1/2003 | Hoffman | A61C 13/275 433/181 |
| 6,902,401 | B2 * | 6/2005 | Jorneus | A61C 8/0048 433/172 |
| 6,974,322 | B2 * | 12/2005 | May | A61C 8/0048 433/172 |
| 7,040,895 | B2 * | 5/2006 | Davis | A61C 13/24 433/185 |
| 7,059,854 | B2 * | 6/2006 | Wu | A61C 8/0069 433/172 |
| 7,214,061 | B2 * | 5/2007 | Fortin | A61C 13/275 433/173 |
| 7,806,691 | B2 * | 10/2010 | Berger | A61C 13/275 433/167 |
| 8,128,706 | B2 * | 3/2012 | Kaigler, Sr. | A61C 8/0006 623/23.57 |
| 8,529,260 | B2 * | 9/2013 | Berger | A61C 8/0048 433/172 |
| 8,739,350 | B1 | 6/2014 | Lackenbauer | |
| 8,900,614 | B2 * | 12/2014 | Bardach | A61F 5/0006 424/422 |
| 8,926,325 | B2 * | 1/2015 | Berger | A61C 8/0048 433/172 |
| 9,017,074 | B2 * | 4/2015 | Boe | A61C 13/01 433/171 |
| 9,055,993 | B2 * | 6/2015 | Grobbee | A61C 13/2656 |
| 9,113,986 | B2 * | 8/2015 | Shima | A61C 13/01 |
| 9,301,816 | B2 * | 4/2016 | Kaigler, Sr. | A61C 8/0006 |
| 2004/0038181 | A1 * | 2/2004 | Fortin | A61C 13/275 433/173 |
| 2006/0040235 | A1 * | 2/2006 | Davis | A61C 13/24 433/185 |
| 2006/0228673 | A1 * | 10/2006 | Fenc | A61C 3/00 433/188 |
| 2009/0325125 | A1 * | 12/2009 | DiAngelo | A61C 8/0001 433/173 |
| 2011/0236856 | A1 * | 9/2011 | Kanazawa | A61C 13/1003 433/199.1 |
| 2012/0276502 | A1 * | 11/2012 | Marshall | G05B 19/4099 433/199.1 |
| 2014/0272797 | A1 * | 9/2014 | Prestipino | A61C 13/34 433/199.1 |
| 2015/0064653 | A1 * | 3/2015 | Grobbee | A61C 13/2656 433/199.1 |
| 2015/0147723 | A1 * | 5/2015 | Berger | A61C 8/0048 433/199.1 |
| 2015/0230891 | A1 * | 8/2015 | Grobbee | A61C 13/225 433/199.1 |

* cited by examiner

DENTAL PROSTHESIS WITH SEALED ATTACHMENT INTERFACE AND CLEANING FLUID ACCESS THERETO

FIELD OF INVENTION

The present invention relates to permanent dental prosthesis attached via attachment posts. In particular, the present invention relates to permanent dental prosthesis with cleansing fluid access to the attachment interface.

BACKGROUND OF INVENTION

Permanent dental prostheses are commonly monolithic units for the upper and lower teeth rows. Such dental prostheses are attached to a number of arbor implants that is only a fraction of the number of teeth in each prosthesis. Due to the low number of such arbors, their surgical implantation into a patient's gums is much less invasive and also more cost effective.

The attachment interface of such Prior Art dental prostheses requires a gap between the artificial gum of the prosthesis and the patient's gum. This gap is necessary to access the arbor and attachment posts for cleaning and to prevent building up of residual food particles and bacteria between the artificial gums and the patient's gums. Nevertheless, this gap is esthetically displeasing as it may become visible during a patient's smile. Moreover, the gap tends to produce a whistling or hissing sound during speaking. Also, the gap needs to be accessed along its entire length for cleaning, which may be difficult for a patient of advanced age and reduced arm and hand mobility. Therefore, there exists a need for a dental prosthesis with a sealed attachment interface and a fluid cleansing system that is simple and reliable to operate. The present invention addresses these needs.

SUMMARY

A dental prosthesis of the present invention features a gum sealing rim that extends towards the patient's gum and snuggly contacts it. The cavity formed within the gum sealing rim is accessed by through holes that extend at the peripheral side of the dental prosthesis across the gum sealing rim. Via the access holes, a pressurized cleaning fluid may be conveniently injected into the cavity. Dental pressure cleaners are well known in the art to provide such pressurized cleaning fluid via a handheld nozzle. Such handheld nozzle is simply held against one of the cleaning fluid access while the pressurized fluid is injected with high velocity. Inside the cavity, the cleaning fluid swirls around and washes off bacteria and deposits. Through a number of cleaning fluid drains, the cleaning fluid exits again the cavity.

An additional drain blocker may be employed to block the cleaning fluid drains. For that purpose, the drain blocker may be configured such that it blocks the cleaning fluid drains while it is clamped by the patient between the teeth. The resulting pressure build up in the cavity causes the cleaning fluid to squeeze out and clean the sealing interface between the gum sealing rim and the patient's gum.

DETAILED DESCRIPTION

Figure 1:
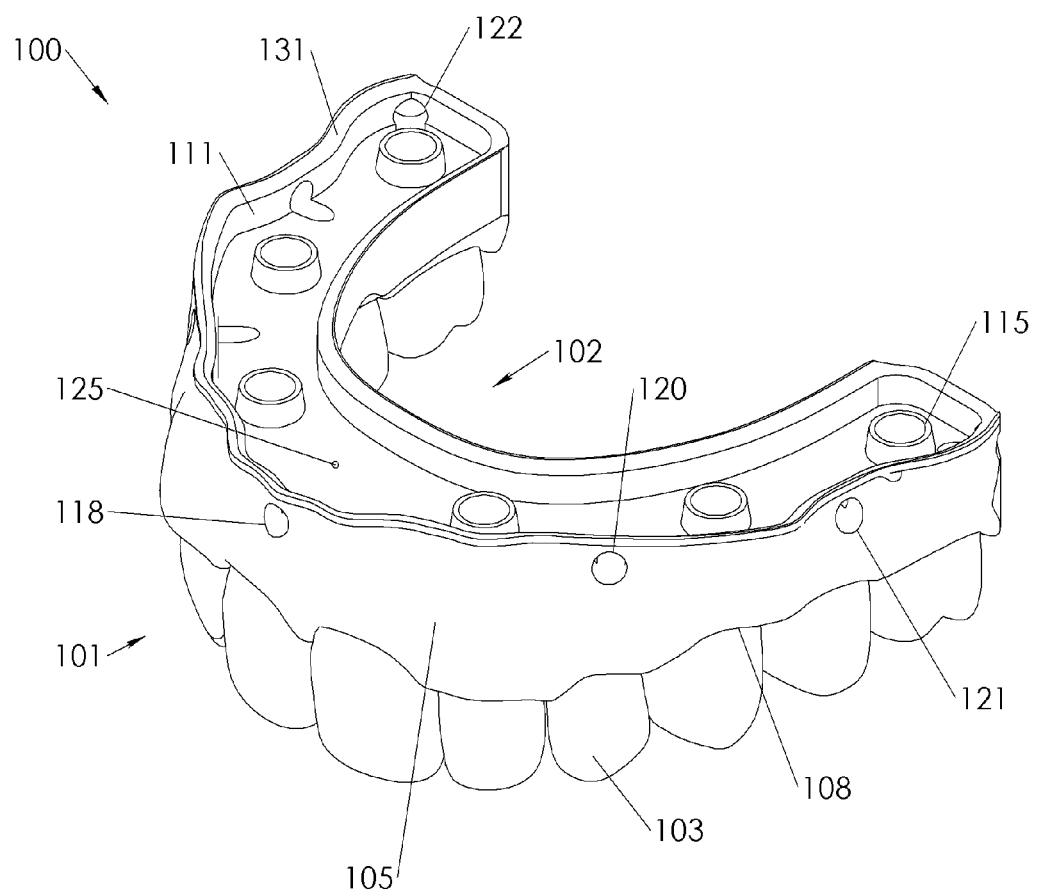
FIG. 1 is a perspective view of a dental prosthesis of the present invention.

Referring to FIG. 1, a dental prosthesis 100 of the present invention may have a peripheral side 101 and a central side 102. The dental prosthesis 100 may have a number of artificial teeth 103 embedded in an artificial gum 105. Artificial teeth 103 and artificial gum 105 are separated by an artificial gum line 108. At the attachment side of the dental prosthesis 100 that is opposite the teeth 103 are a number of attachment posts 115 as is well known in the art.

The dental prosthesis 100 features at least one cleaning fluid access 118 and at least one but preferably a number of cleaning fluid drains 120, 121, 122. The cleaning fluid drains 120, 121, 122 are preferably on the peripheral side 101 and above the artificial gum line 108. The dental prosthesis 100 features also a gum sealing rim 111 across which are extending the cleaning fluid access 118 and cleaning fluid drains 120, 121, 122 in the preferred form of through holes.

Figure 2:
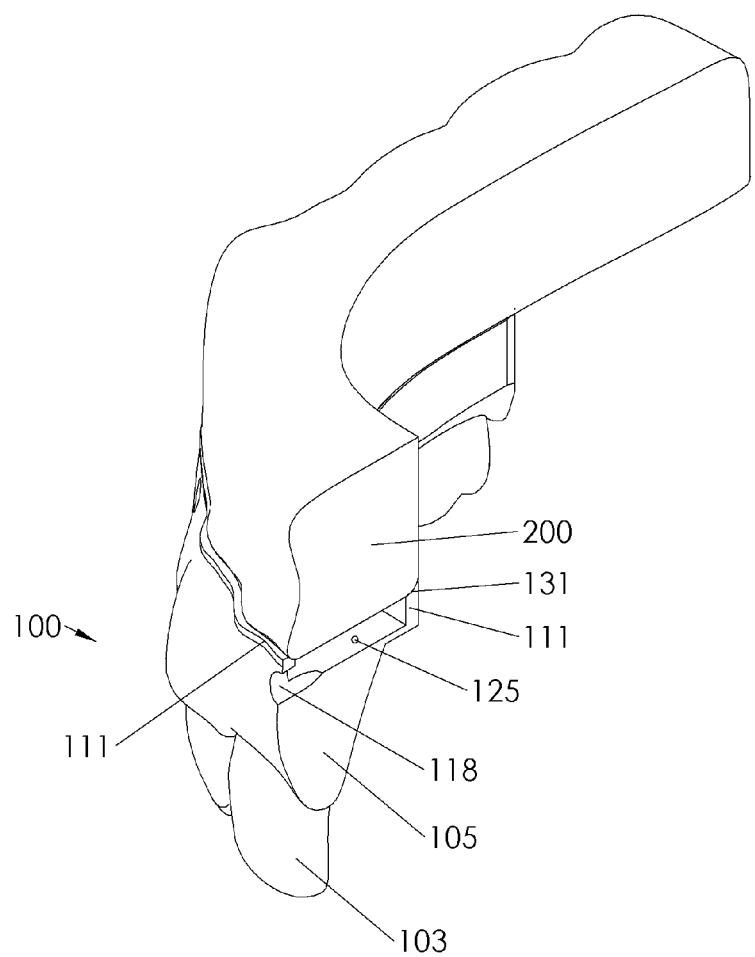
FIG. 2 is a perspective cut view of the dental prosthesis of FIG. 1 and a patient's gum.
Figure 3:
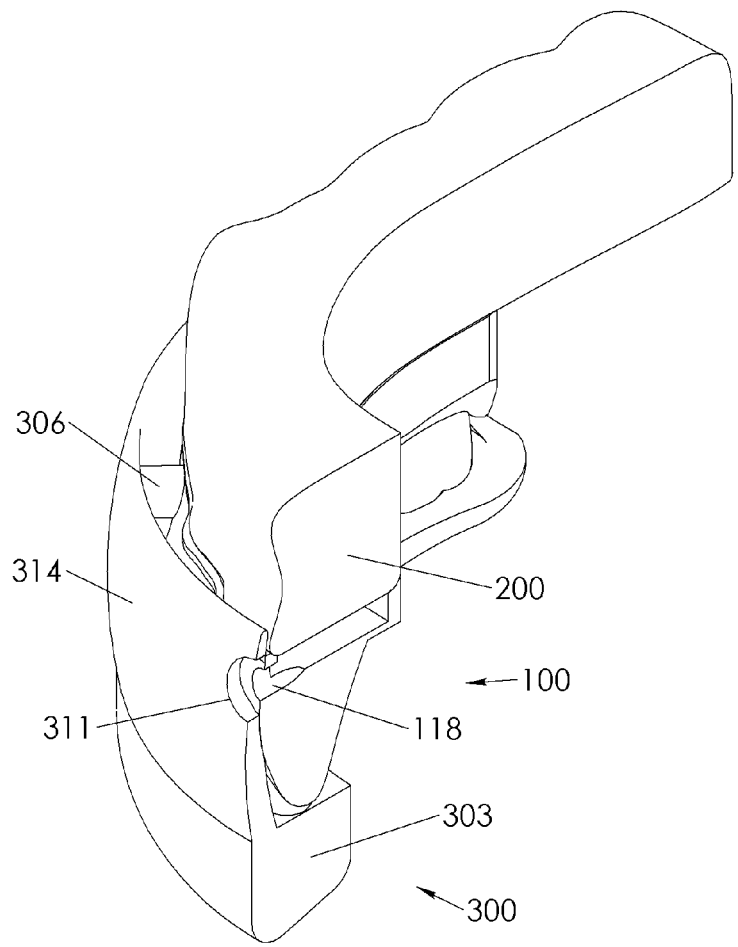
FIG. 3 is the perspective cut view of the dental prosthesis and the patient's gum of FIG. 2 and a drain blocker.

As shown in FIGS. 2, 3, the gum sealing rim 111 forms a gum sealing interface 131 with a patient's attachment gum 200 while the dental prosthesis 100 is attached thereto via the attachment posts 115 as is well known in the art. A cleaning fluid cavity 125 that is within the gum sealing rim 111 is also in between the dental prosthesis 100 and the attachment gum 200 while the dental prosthesis 100 is attached to the patient's attachment gum 200. The cleaning fluid access 118 and cleaning fluid drains 120, 121, 122 become thereby preferably the sole access to peripherally communicate cleaning fluid to and from the cleaning fluid cavity 125 while the dental prosthesis 100 is attached to the attachment gum 200.

Figure 4:
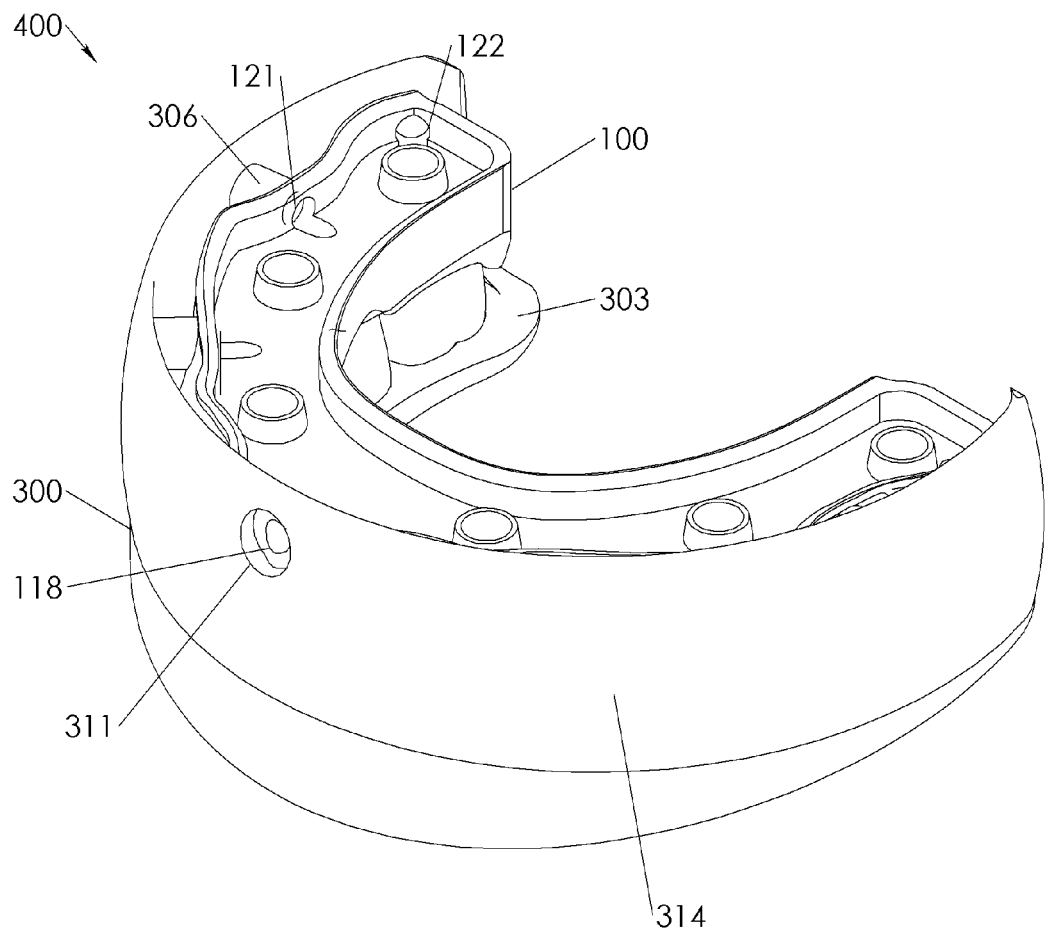
FIG. 4 is the perspective view of the dental prosthesis and the drain blocker of FIG. 3.
Figure 5:
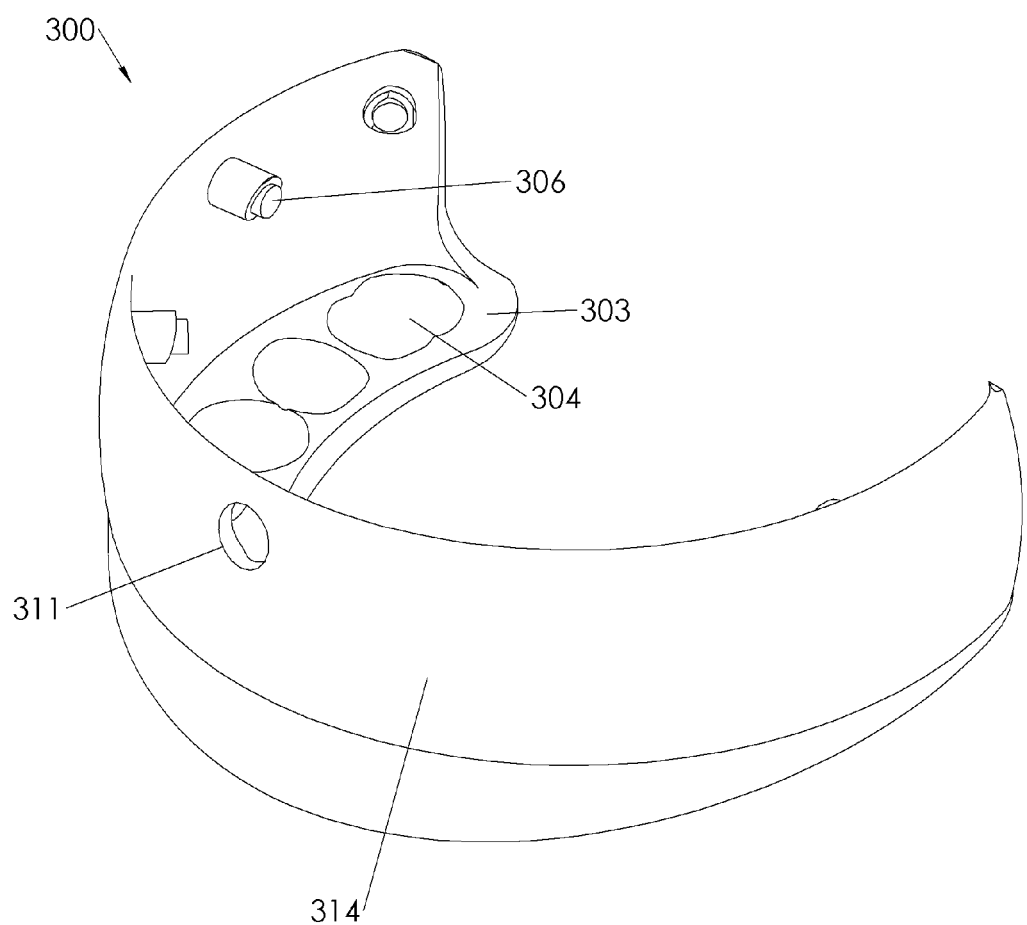
FIG. 5 is the perspective view of the drain blocker of FIGS. 2, 3.

As shown in FIG. 4, the dental prosthesis 100 may be part of a dental prosthesis cleaning system 400 that also includes a drain blocker 300. The drain blocker 300 is configured in conjunction with the cleaning fluid drains 120, 121, 122 such that preferably all cleaning fluid drains 120, 121, 122 are blocked while the drain blocker 300 is in operational position. The drain blocker 300 may have a teeth clamp base 303 that is configured in conjunction with a number of the artificial teeth 103 such that the drain blocker 300 is in operational position and blocking the cleaning fluid drains 120, 121, 122 while the teeth clamp base 303 is clamped down by the artificial teeth 103. For that purpose, the teeth clamp base 303 may feature teeth sockets 304.

The drain blocker 300 may feature a number of drain plugs 306 in a number that is preferably equal to the number of cleaning fluid drains 120, 121, 122. The drain plugs 306 are shaped in conjunction with the cleaning fluid drains 120, 121, 122 such that they are plugging them while the drain blocker 300 is in operational position.

The drain blocker 300 may further feature a blocker rim 314 that may extend above the gum sealing interface 131 while the drain blocker 300 is in operational position. While the drain blocker 300 is in operational position with the cleaning fluid drains 120, 121, 122 plugged, cleaning fluid is pressurized accessed to the cleaning fluid access 118 across a cleaning access 311 of the drain blocker 300. The pressurized cleaning fluid that consequently builds up in the cleaning fluid cavity 125, squeezes out through the gum sealing interface 131. The blocker rim 314 extending above the gum sealing interface 131 may keep the squeezed out cleaning fluid in the proximity of the dental prosthesis 100.

The dental prosthesis 100 with all its described inventive features may be fabricated and attached to the patient's gum 200 with well known techniques. Once attached, the gum sealing rim 111 is in a snug fit with the attachment gum 200. During regular cleaning of the dental prosthesis 100, a well known commercially available pressurized fluid dental cleaner may be employed to clean the artificial teeth 103 and artificial gum 105. During the course of such cleaning operation, the well known nozzle of such pressurized fluid dental cleaner may be positioned at the cleaning fluid access 118 initially without the drain blocker 300 in place. The injected cleaning fluid washes the cleaning fluid cavity 125 and exits via the cleaning fluid drains 120, 121, 122. Next, the drain blocker 300 is put into operational position and cleaning fluid is again injected into the previously cleaned cavity 125. The cleaning fluid builds up pressure inside the cleaning fluid cavity 125 since the cleaning fluid drains 120, 121, 122 are now blocked. Eventually the cleaning fluid pressure breaks through the gum sealing interface 131 and rinses the gum sealing interface 131 as well.

Accordingly, the scope of the invention described in the Figures and Specification above is set forth by the following claims and their legal equivalents:

What is claimed is:

1. A dental prosthesis comprising a cleaning fluid access, further comprising a gum sealing rim forming a gum sealing interface with a patient's attachment gum and wherein said cleaning fluid access extends across said gum sealing rim.

2. The dental prosthesis of claim 1, wherein said cleaning fluid access is a through hole.

3. The dental prosthesis of claim 1, comprising a cleaning fluid drain, wherein said cleaning fluid drain is a through hole.

4. A dental prosthesis comprising:
   A. a gum sealing rim forming a gum sealing interface with a patient's attachment gum;
   B. a cleaning fluid cavity that is within said gum sealing rim and that is in between said dental prosthesis and a patient's attachment gum while said dental prosthesis is attached to said a patient's attachment gum; and
   C. a cavity access to peripherally communicate cleaning fluid at least one of to and from said cleaning fluid cavity while said dental prosthesis is attached to said a patient's attachment gum.

5. The dental prosthesis of claim 4, wherein said cavity access is on the peripheral side of said dental prosthesis.

6. The dental prosthesis of claim 4, wherein said cavity access is above an artificial gum line of said dental prosthesis.

7. The dental prosthesis of claim 4, wherein said cavity access extends across said gum sealing rim.

8. The dental prosthesis of claim 7, wherein said cavity access is a through hole.

9. A dental prosthesis cleaning system comprising:
   A. a dental prosthesis comprising a cleaning fluid access and a cleaning fluid drain; and
   B. a drain blocker configured in conjunction with said cleaning fluid drain such that said cleaning fluid drain is blocked while said drain blocker is in operational position.

10. The dental prosthesis cleaning system of claim 9, wherein said drain blocker has a teeth clamp base that is configured in conjunction with at least one tooth of said dental prosthesis such that said drain blocker is blocking said cleaning fluid drain while said teeth clamp base is clamped down by said at least one tooth.

11. The dental prosthesis cleaning system of claim 9, wherein said drain blocker comprises a drain plug that is plugging said cleaning fluid drain while said drain blocker is in operational position.

12. The dental prosthesis cleaning system of claim 9, wherein said drain blocker further comprises a blocker rim that is extending above a gum sealing interface between said dental prosthesis and a patient's attachment gum while said drain blocker is in operational position.

13. The dental prosthesis cleaning system of claim 9, wherein said drain blocker further comprises a cleaning access.

* * * * *